(12) United States Patent
Abrahamson et al.

(10) Patent No.: US 8,938,305 B2
(45) Date of Patent: Jan. 20, 2015

(54) MEDICAL TRANSCEIVER DEVICE AND METHOD

(75) Inventors: Hans Abrahamson, Stockholm (SE); Tomas Snitting, Stockholm (SE)

(73) Assignee: St. Juse Medical AB, Jarfalla (SE)

( * ) Notice: Subject to any disclaimer, the term of this patent is extended or adjusted under 35 U.S.C. 154(b) by 2329 days.

(21) Appl. No.: 11/597,968

(22) PCT Filed: May 28, 2004

(86) PCT No.: PCT/SE2004/000832
§ 371 (c)(1),
(2), (4) Date: Jan. 3, 2008

(87) PCT Pub. No.: WO2005/115541
PCT Pub. Date: Dec. 8, 2005

(65) Prior Publication Data
US 2008/0288024 A1     Nov. 20, 2008

(51) Int. Cl.
*A61N 1/372*     (2006.01)
*H01Q 1/22*     (2006.01)
*H04B 7/10*     (2006.01)

(52) U.S. Cl.
CPC .............. *H01Q 1/22* (2013.01); *A61N 1/37223* (2013.01); *H04B 7/10* (2013.01); *A61N 1/37229* (2013.01)
USPC .................................. 607/60; 607/30; 607/32

(58) Field of Classification Search
CPC .................................................. A61N 1/37223
USPC .................. 128/903; 600/300; 607/30, 32, 60
See application file for complete search history.

(56) References Cited

U.S. PATENT DOCUMENTS

| | | | |
|---|---|---|---|
| 6,167,312 A | 12/2000 | Goedeke | |
| 6,169,925 B1 | 1/2001 | Villaseca et al. | |
| 6,456,245 B1 * | 9/2002 | Crawford | 343/702 |
| 6,463,329 B1 | 10/2002 | Goedeke | |
| 6,659,947 B1 * | 12/2003 | Carter et al. | 600/300 |
| 2004/0106967 A1 * | 6/2004 | Von Arx et al. | 607/60 |
| 2004/0212496 A1 * | 10/2004 | Villaseca et al. | 340/539.12 |

* cited by examiner

*Primary Examiner* — Carl H Layno
*Assistant Examiner* — Jennifer Ghand

(57) ABSTRACT

A medical transceiver device for radio-based communication with an implantable medical device has circuitry for transmitting radio-frequency signals to, and/or receiving radio-frequency signals from, the implantable medical device, first and second electrically conductive structures, and an antenna feed network operatively interconnected between the circuitry and the first and second conductive structures. Each of the first and second conductive structures is operable as a transmitting and/or receiving antenna for the radio-frequency signals. The first and second conductive structures emit and/or receive radio waves of different polarizations, and the first and second conductive structures are disposed adjacent each other at a single location in space, thereby providing spatial diversity that is independent of the polarization diversity.

41 Claims, 3 Drawing Sheets

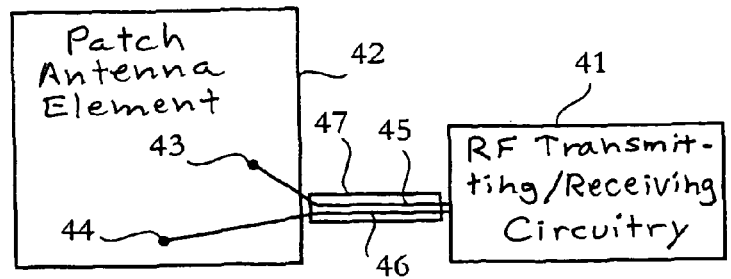
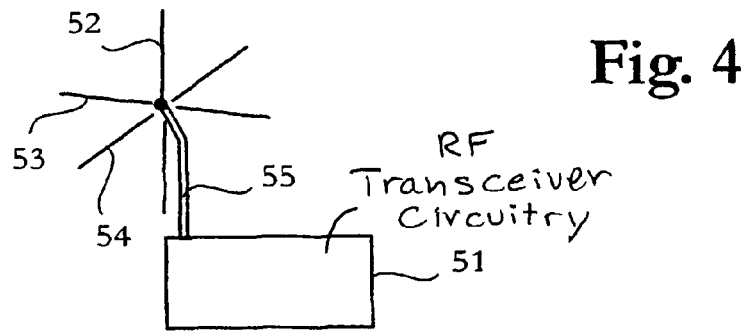
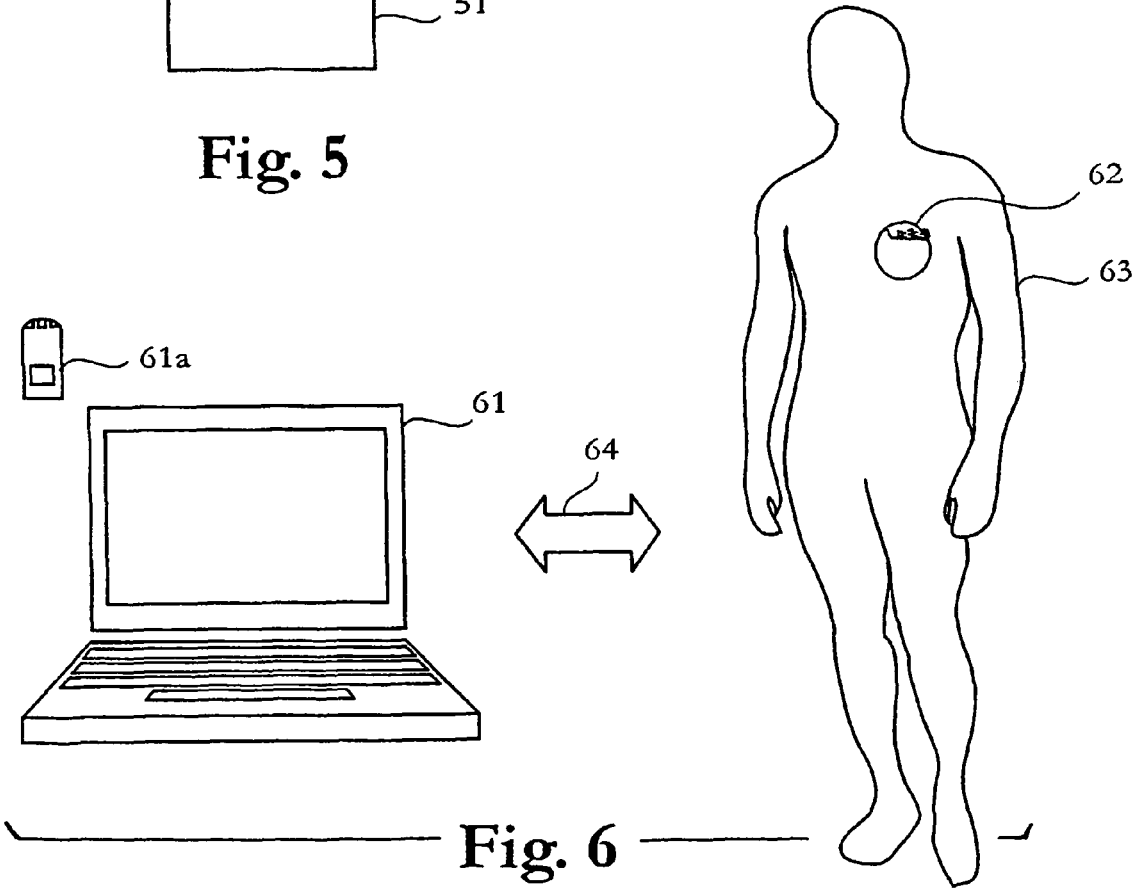

MEDICAL TRANSCEIVER DEVICE AND METHOD

BACKGROUND OF THE INVENTION

1. Field of the Invention

The present invention relates to a medical transceiver device and a method, respectively, for radio-based communication with an implantable medical device, and to a system comprising the medical transceiver device and the implantable medical device.

2. Description of the Prior Art

In the context of implantable medical devices, it has become common to provide a communication link between the implanted device and an external programmer or monitor in order to allow for transmission of commands from the external device to the implanted device and to allow for transmission of stored information and/or sensed physiological parameters from the implanted device to the external programmer. Conventionally, communication between an implanted device and an external programmer has been accomplished by means of a telemetry system, which includes a transceiver located within the implanted medical device and an external programmer or monitor, also having a transceiver and one or more antennas.

U.S. Pat. Nos. 6,167,312 and 6,169,925 disclose such medical communication systems, the contents of which being incorporated herein by reference.

The former patent describes a device for use in communication with an implantable medical device, which is provided with a spatial diversity antenna array mounted to the device housing and an operating at defined frequency, located within the device housing, coupled to the antenna array. The antenna array includes at least one antenna permanently mounted to the device housing and an antenna removably mounted to the device housing and locatable at a distance from the housing, coupled to the radio frequency transceiver. A device controller selects which of the antennas in the antenna array is coupled to the transceiver responsive to the quality of signals received by the antennas.

The latter patent describes also a spatial diversity antenna array. Here, the antenna array comprises two antennas spaced a fraction of the wavelength of the defined frequency from one another, each antenna including two antenna elements mounted to the housing and located orthogonal to one another. Selection of which of the antennas is employed is accomplished by a device controller, responsive to the quality of the signals received by the antennas.

The patents described above thus address the problem of different signal strengths in space.

Another problem when transferring signals between two antennas is, however, that the receiving antenna will only sense maximum signal strength if its polarization state is similar to the polarization state of the incoming signal. In the case of linearly polarized waves, a simple way to achieve this is to simply rotate the receiving antenna until it is aligned with the field vector of the incoming linearly polarized waves.

A particular problem when transferring radio-based signals between an implantable medical device and an external device is due to the fact that the antenna polarization of the implantable medical device will be arbitrary. Since the antenna of the implantable medical device for several reasons needs to be a small and simple antenna, any system optimization with respect to polarization has to be made to the external communication device.

Neither U.S. Pat. No. 6,167,312 nor U.S. Pat. No. 6,169,925 disclose an external communication device provided with polarization diversity functionality. Even if their antennas would be maximally sensitive to radio frequency signals of different polarization, they are located far from each other, and low received signal strength could depend on position rather than polarization sensitivity of the receiving antenna. The patents provide no solution for determining an optimum polarization state for radio frequency signals to be transmitted to the implantable medical device and/or to be received from there.

SUMMARY OF THE INVENTION

An object of the present invention to provide a medical transceiver device and a method, respectively, for radio-based communication with an implantable medical device, which overcome the above-mentioned problems.

In this respect a particular object of the invention is to provide such a medical transceiver device and method, by which polarization diversity essentially independently of spatial diversity is implementable.

A still further object of the invention is to provide such a medical transceiver device and method, by which an overall improved antenna performance compared to that of prior art devices, is obtainable.

A yet further object of the invention is to provide such a medical transceiver device, which is possible to manufacture to a rather low cost, is easy to tune, and enables an efficient use of available space.

A still further object of the invention is to provide such a medical transceiver device, which is reliable, and particularly mechanically durable.

These objects are achieved in accordance with the present invention by a medical transceiver device for radio-based communication with an implantable medical device, having circuitry for transmitting radio frequency signals to, and/or receiving radio frequency signals from, the implantable medical device, first and second electrically conductive structures, and an antenna feed network operatively interconnected between the circuitry and the first and second conductive structures. Each of the first and second conductive structures is adapted to operate as a transmitting and/or receiving antenna for the radio frequency signals, the first and second conductive structures emit and/or receive radiation of different polarizations, and the first and second conductive structures are provided adjacent each other at a single location in space.

Such a medical transceiver device enables employment of polarization diversity essentially independently of spatial diversity.

The above objects also are achieved in accordance with the invention by a method for radio-based communication with an implantable medical device including the following steps. Radio frequency signals are received from an implantable medical device via first and second antenna structures, which are maximally sensitive to differently, preferably orthogonally, polarized waves and are provided adjacent each other at a single location. The radio frequency signals received via the first and second antenna structures are analyzed, and a polarization state of the received radio frequency signals is determined. Finally, radio frequency signals are transmitted to the implantable medical device via the first and second antenna structures, wherein the amplitude and/or phase of the radio frequency signals transmitted via the first antenna structure relative the amplitude and/or phase of the radio frequency signals transmitted via the second antenna structure are/is selected depending on the determined polarization state.

The above objects also are achieved in accordance with the present invention by a medical communication system having a medical programmer or monitoring device and an implantable medical device. The implantable medical device comprises a radio transmitter and/or receiver, and wherein the medical programmer or monitoring device includes a medical transceiver device as described above.

In the description, it is to be understood that the antenna of the present invention is operable to transmit or receive radio frequency signals. Even when a term is used herein that suggests one specific signal direction, it is to be appreciated that such a situation can cover that signal direction and/or its reverse.

DESCRIPTION OF THE DRAWINGS

FIG. 4 schematically illustrates a second embodiment for arranging the electrically conductive structures in a medical transceiver device according to the invention.

FIG. 5 schematically illustrates a third embodiment for arranging the electrically conductive structures in a medical transceiver device according to the invention.

FIG. 6 schematically illustrates a medical communication system including a medical transceiver device in accordance with the invention and an implantable medical device.

DESCRIPTION OF THE PREFERRED EMBODIMENTS

Figure 1:
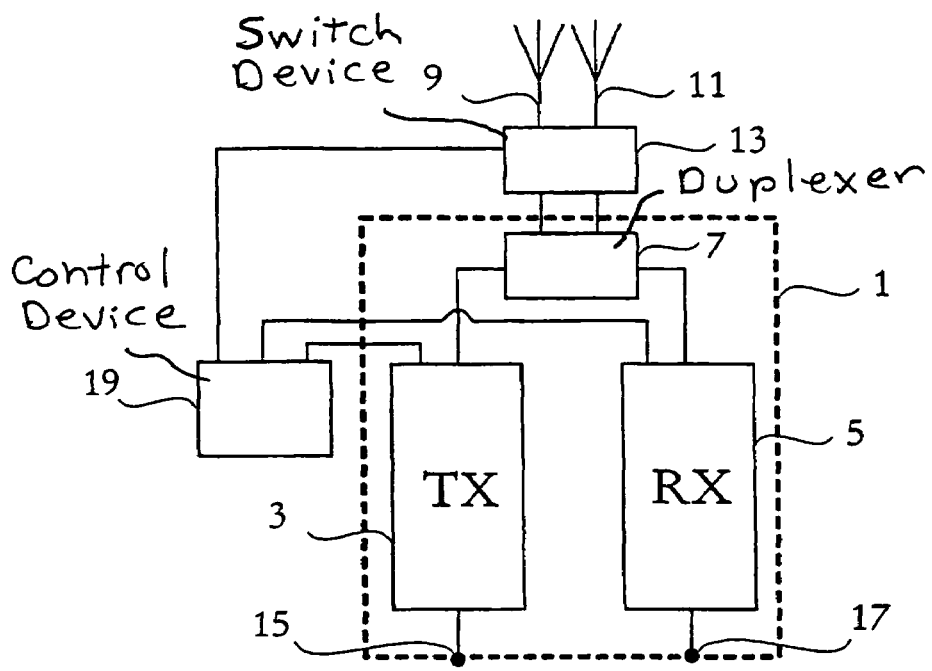
FIG. 1 is a schematic block diagram of a medical transceiver device for radio-based communication with an implantable medical device, according to a first embodiment of the invention.

With reference to FIG. 1, a medical transceiver device for radio-based communication with an implantable medical device according to a preferred embodiment of the present invention comprises circuitry 1 connected to first and second electrically conductive and radiating structures or antennas 9, 11 via a switch device 13. A control device 19 is connected to the circuitry 1 and to the switch device 13.

The circuitry 1, which comprises transmitter 3 and receiver 5 sections connected to the switch device 13 and electrically conductive structures 9, 11 via a duplexer 7, is a high frequency part of the medical transceiver device provided for transmitting radio frequency signals to, and receive radio frequency signals from, an implantable medical device (not illustrated) via the first and second radiating structures 9, 11.

Thus, the circuitry 1 is preferably arranged to be electrically connected, via radio communications circuitry, to a digital or analog signal processor of the medical transceiver device. The control device 19 may be an integral part of this signal processor, or may be a separate device, optionally connected to the signal processor.

The medical transceiver device 1 is preferably arranged on a carrier (not shown), which may be a flexible substrate, a MID (molded interconnection device) or a PCB (printed circuit board).

The transmitter section 3 includes an input 15 for receiving signals from a transmitting source of the medical transceiver device, and circuitry for transforming the received signals to radio frequency signals, which are then fed to the first and second radiating structures 9, 11 via the duplexer.

Correspondingly, the receiver section 5 includes circuitry for receiving radio frequency signals via the first and second electrically conductive structures 9, 11, and the duplexer 7, and for forming signals, which are then output at 17 to other circuitry of the medical transceiver device.

The circuitry 1 is operatively connected to the first and second radiating structures 9, 11 via respective transmission lines, which typically include an antenna feeding and impedance matching network (not illustrated in FIG. 1).

The switch device 13 connected in the transmission lines is switchable between at least two antenna configuration states. In the first antenna configuration state only the first radiating structure 9 is operatively connected to the circuitry 1 via the duplexer 7, and in the second antenna configuration state only the second radiating structure 11 is operatively connected to the circuitry 1. The switch device 13 is optionally switchable to third and fourth antenna configuration states, in both of which both the first and the second radiating structures 9, 11 are operatively connected to the circuitry 1. However, in the fourth antenna configuration state, a 180° phase shifter is connected to introduce a 180° phase shift to the radio frequency signals as transmitted via either one of the first and the second radiating structures 9, 11.

Each of the first and second radiating structures 9, 11 is adapted, individually and jointly, to operate as a transmitting and receiving antenna for the radio frequency signals. The first and second radiating structures or antennas 9, 11 can be of virtually any kind, but they emit and receive radio waves of different, preferably essentially orthogonal, polarizations. Further, they are provided adjacent each other at a single location in space to thereby enable the employment of polarization diversity essentially independently of spatial diversity.

The first and second radiating structures 9, 11 may be separated by less than the maximum length of either one of the first and second radiating structures 9, 11, more preferably less than ¼ of the maximum length of either one of the first and second radiating structures 9, 11, and still more preferably less than ⅛ of the maximum length of either one of the first and second radiating structures 9, 11. For instance, if the first and second radiating structures 9, 11 are each a linear antenna having a length of e.g. 12 cm, the separation (i.e. shortest distance) between the linear antennas is less than 12 cm, more preferably less than 3 cm, and still more preferably less than 1.5 cm.

The separation of the first and second radiating structures 9, 11 may be expressed in terms of the wavelength of the radio frequency signals as follows. The first and second radiating structures 9, 11 may be separated by less than a quarter of the wavelength of the radio frequency signals, more preferably less than ⅛ of the wavelength of the radio frequency signals, and still more preferably less than 1/16 of the wavelength of the radio frequency signals.

In an ideal case to enable polarization diversity completely independently of spatial diversity, the first and second radiating structures or antennas 9, 11 should be located at a single common point in space. However, since this is not feasible, the antennas are advantageously provided as close to each other as possible.

The control device 19 comprises, or is connected to, a measuring device provided for measuring a signal quality parameter of the received radio frequency signals as received by each of the first and second radiating structures 9, 11, and is provided to control the switch device 13 to switch to an antenna configuration state, in which either one of the first and second radiating structures 9, 11 is connected to the circuitry 3 for signals depending on the measured signal quality parameter of the radio frequency signals as received by each of the first and second radiating structures 9, 11. The signal quality parameter may e.g. be any of signal strength, bit error rate (BER), carrier-to-noise (C/N) ratio, carrier-to-interference (C/I) ratio, or received signal strength indicators (RSSI).

Preferably, the control device 19 is provided to control the switch device 13 to switch to the antenna configuration state, in which the one of the first and second radiating structures 9, 11 that receives the best signal quality parameter, for the subsequent reception of radio frequency signals. By best signal quality parameter is meant the signal quality parameter that indicates the best antenna performance, e.g. highest signal strength, lowest bit error rate, highest received signal strength indicators, etc.

If the third and fourth antenna configuration states are available, the control device 19 may control the switch device 13 to switch to any of these antenna configuration states provided that it is measured as being favorable for subsequent reception.

Similarly, the control device 19 is preferably provided to control the switch device 13 to switch to a similar antenna configuration state for subsequent transmission of radio frequency signals.

Alternatively or additionally, the measuring device is provided for measuring a phase of the received radio frequency signals as received by each of the first and second radiating structures 9, 11, and the control device 19 is provided to control the switch device 13 to switch to one of the antenna configuration states for subsequent reception and/or transmission of radio frequency signals depending on the measured phases of the radio frequency signals as received by each of the first and second radiating structures 9, 11.

Figure 2:
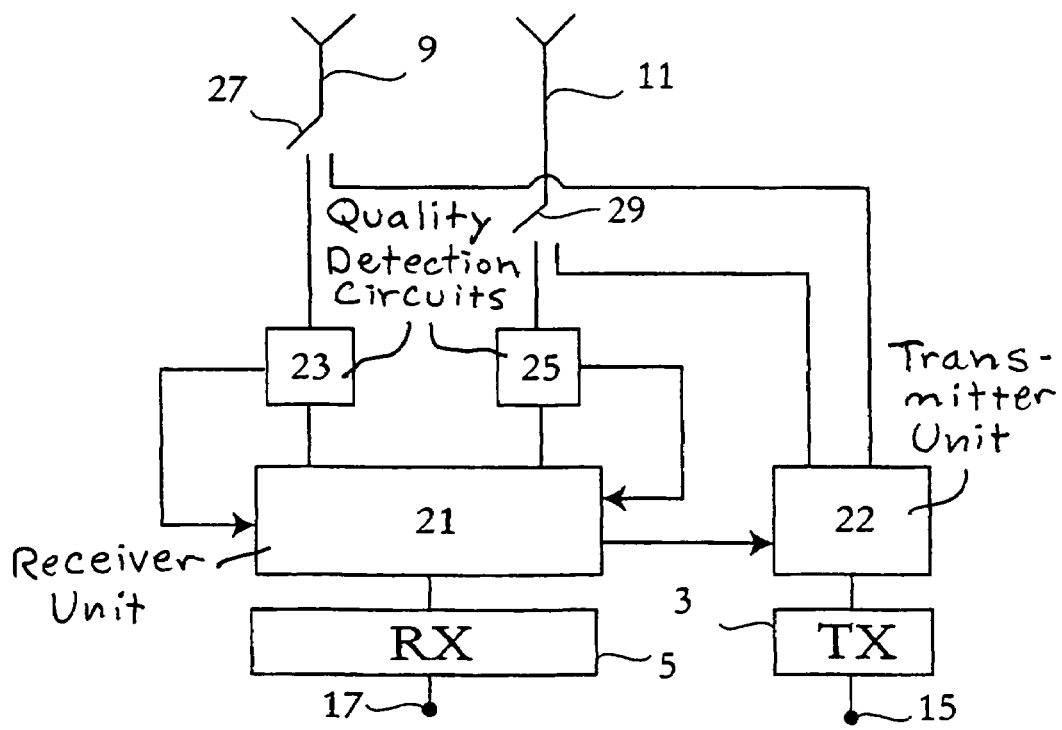
FIG. 2 is a schematic block diagram of a medical transceiver device for radio-based communication with an implantable medical device, according to a second embodiment of the invention.

With reference next to FIG. 2, a medical transceiver device for radio-based communication with an implantable medical device according to a further preferred embodiment of the invention comprises a receiver unit 21 and signal quality detection units 23, 25 connected between the receiver section 5 and the first and second radiating structures 9, 11, and a transmitter unit 22 connected between the transmitter section 3 and the first and second radiating structures 9, 11. Switching units 27, 29 are provided for switching the first and second radiating structures 9, 11 between reception and transmission modes.

The signal quality detection units 23, 25 are provided for detecting a signal quality parameter of radio frequency signals as received by each of the first and second radiating structures 9, 11.

The receiver unit 21 is provided for weighted summing of the radio frequency signals as received by the first and second radiating structures 9, 11 based on the measured signal quality parameter of the received radio frequency signals, and optionally for co-phasing the radio frequency signals (i.e. phase shifting the radio frequency signals to obtain a 0° phase difference between the signals) received from the first and second radiating structures 9, 11. Hereby, a signal can be formed from the radio frequency signals received from the first and second radiating structures 9, 11, which has a better signal quality than either one of the radio frequency signals received from the first and second radiating structures 9, 11.

The receiver unit 21 is connected to the transmitter unit 22 to provide the transmitter unit 22 with the measured signal quality parameter of the radio frequency signals received by the first and second radiating structures 9, 11. The transmitter unit 22, which includes amplitude attenuating and phase shifting circuitry, is then provided to alter the amplitude and the phase of radio frequency signals that are to be transmitted. Preferably, the amplitude or signal strength and the phase of the radio frequency signals that are to be transmitted by at least one of the first and second radiating structures 9, 11 are altered depending on the measured signal qualities and phases of the radio frequency signals as received by each of the first and second radiating structures 9, 11 during the measurement performed by the signal quality detection units 23, 25.

Preferably, the transmitter unit 22 is provided to alter the signal strength and the phase of the radio frequency signals to be transmitted by at least one of the first and second radiating structures 9, 11 to thereby achieve a combined output of the radio frequency signals to be transmitted, which has a polarization similar to the polarization of a combined input of the radio frequency signals as received via the first and second electrically conductive structures 11, 13 during the measurement by the signal quality detection units 23, 25.

Alternatively, the medical transceiver device and the control device thereof receives from the implantable medical device a measure of a signal quality parameter of radio frequency signals as received by the implantable medical device, wherein the radio frequency signals received by the implantable medical device are radio frequency signals as transmitted from the medical transceiver device to the implantable medical device after having been distorted by a transmission medium, i.e. the air interface between the antennas of the respective devices.

The transmitter unit 22 can then be provided to alter the signal strength and the phase of the radio frequency signals as subsequently transmitted by at least one of the first and second radiating structures 9, 11 depending on the received measure of the signal quality parameter of the radio frequency signals as received by the implantable medical device.

Figure 3:
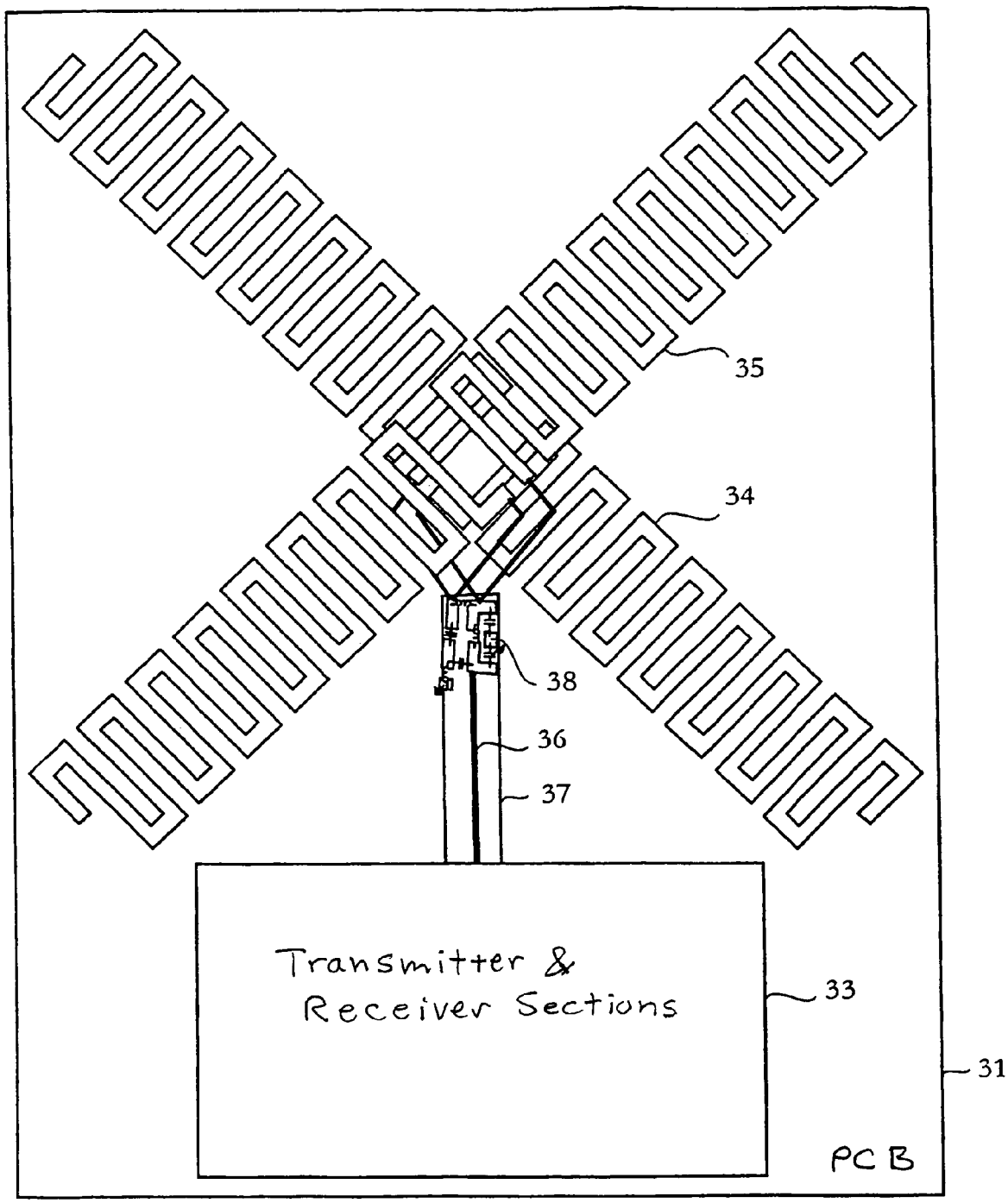
FIG. 3 schematically illustrates a first embodiment for arranging the electrically conductive structures in a medical transceiver device according to the invention.

With reference next to next to FIG. 3, a medical transceiver device for radio-based communication with an implantable medical device according to a particular embodiment of the invention comprises a PCB 31, on which the circuitry comprising the transmitter and receiver sections, here denoted by 33 and the two radiating structures, here denoted by 34 and 35, are arranged and operatively interconnected via a transmission line 36, 37 and transmission or feeding circuitry 38.

Each of the first and second radiating structures 34, 35 includes an electrically short and meander shaped dipole antenna, preferably made of a wire or a strip printed on the PCB 31. The inductive meander shape infers inductance to compensate for the high capacitance associated with the antenna.

The antennas 34, 35 are arranged in a crossed relationship (i.e. rotated 90° relative each other) on top of each other in an electrically insulated manner. In such a manner the antennas 34, 35 produce essentially linearly polarized radio frequency signals, which are essentially orthogonal to each other. Preferably, the mass centers of the antennas 34, 35 are located along a straight line orthogonal to the plane of extensions of the antennas 34, 35, which is as short as possible. Preferably, the antennas 34, 35 are separated by a thin layer of a dielectric material.

The transmission line 36, 37 is preferably a standard microstrip transmission line including a conductive strip 36 over a grounding strip 37. The grounding strip needs to have width in the order of ten times the width of the strip.

The circuitry 33 is provided for producing radio frequency signals as unbalanced signals, which are fed via the transmission line 36, 37 towards the dipole antenna elements 34, 35. However, since the dipole antenna elements 34, require a balanced feeding, the transmission or feeding circuitry 38 includes a Balun provided to transform the unbalanced radio frequency signals to a balanced feeding before being fed to the dipole antenna elements 34, 35 for transmission, and vice versa for reception of radio frequency signals. The Balun comprises typically a number of discrete inductors and capacitors. The Balun transforms also the transmission line impedance of 50 Ohm to the antenna impedance resistance, which may e.g. be in the range of 15 Ohm.

Further, the circuitry 33 includes a control device like any of the control devices 19, 21 as described with reference to FIGS. 1-2 and depending on the control device included, the transmission or feeding circuitry 38 includes a switch device like the switch device 13 of FIG. 1, or an amplitude attenuating unit and a phase shifting unit like the amplitude attenuating unit 23 and the phase shifting unit 25 of FIG. 2. The operation of the medical transceiver device may be similar to the operation of any of the medical transceiver devices of FIGS. 1-2.

It shall be noted that the term "first and second electrically conductive or radiating structures" as used throughout this description does not necessarily indicate that the structures are separated structures. For instance, the first and second electrically conductive or radiating structures may have at least one electrically conductive element in common.

With reference to FIG. 4, a medical transceiver device according to still a further preferred embodiment of the invention comprises circuitry 41 provided for transmitting radio frequency signals to, and/or receiving radio frequency signals from, an implantable medical device. The circuitry is operatively connected to a single patch antenna element 42 via a double transmission line 45-47. The double transmission line 45-47 comprises first and second conductive strips 45, 46 over a wider grounding strip 47. The first conductive strip 45 connects to the single patch antenna element 42 at a first feed or connection point 43 and the second conductive strip 45 connects to the single patch antenna element 42 at a second feed or connection point 44, which is remotely located from the first feed or connection point 43. Preferably, the first and second feed or connection points 43, 44 are arranged close to two orthogonal and adjacent sides of the single patch antenna element 42, which has advantageously a quadratic shape.

Thus, the first and second electrically conductive structures are identical except for having differently located feed or connection points 43, 44 to the double transmission line 45-47.

The circuitry 41 may comprise one or several of the switches, amplitude attenuating units, phase shifting unit, Baluns, impedance matching networks, and control devices as described with reference to the previous embodiments of the present description, and the medical transceiver device of FIG. 4 may be operated similar to any of the medical transceiver devices of those embodiments.

With reference to next to FIG. 5 a medical transceiver device for radio-based communication with an implantable medical device according to yet a further preferred embodiment of the invention differs from the previous embodiment in that the circuitry, here denoted by 51, is operatively connected to three electrically conductive and radiating structures 52-54 via a transmission line 55, which comprises a separate feeding for each of the three radiating structures 52-54.

The three radiating structures 52-54 emit and/or receive radio waves having different, preferably mutually orthogonal, polarizations, and are located adjacent each other at the single location.

The three radiating structures 52-54 can be switched in and out independently of each other, and they can be fed by radio frequency signals of different amplitudes and/or phases in a similar manner as the previous embodiments of the present description.

Thus, by means of the medical transceiver device of FIG. 5 polarization diversity can be employed in three different directions essentially independently of spatial diversity.

Finally, with reference to FIG. 6 a medical communication system comprising a medical programmer or monitoring device 61 and an implantable medical device 62, which is implanted in a patient 63. The implantable medical device 62 comprises a radio transceiver and the medical programmer or monitoring device 61 comprising any of the medical transceiver devices as disclosed in the present description. The radio transceiver of the implantable medical device 62 and the medical transceiver device of the medical programmer or monitoring device 61 are provided for radio-based communication with each other, preferably both-way communication as being indicated by the bidirectional arrow 64.

It shall be noted that the implantable medical device 62 and the medical programmer or monitoring device 61 are typically located in a common room or location. Preferably, the distance between the implantable medical device 62 and the medical programmer or monitoring device 61 is between 0.5 and 20 m, more preferably between 0.5 and 10 m, and most preferably between 1 and 7 m.

In one version, the medical programmer or monitoring device 61 comprises a computer-based device provided with a screen and a keyboard. In such instance, the medical transceiver device may be arranged coplanar with, and close to, the screen of the medical programmer or monitoring device 61.

Further, the first and second electrically conductive and radiating structures of the medical transceiver device may be movable as a unit to thereby provide for spatial diversity.

Such spatial diversity may advantageously be implemented by means of the medical transceiver device being provided as a mobile unit 61*a*, which may be a handhold device, communicating with the medical programmer or monitoring device 61 via a wire or wirelessly. Preferably, the mobile unit 61*a* is provided with a processor and memory in order to communicate with the medical programmer or monitoring device 61 via USB, Bluetooth, or infrared connections.

In an alternative version of the system the medical transceiver device of FIG. 3 may be movable with respect to the medical programmer or monitoring device 61, e.g. it may slidable in a groove of the medical programmer or monitoring device 61 intended therefore.

Alternatively, the medical programmer or monitoring device 61 may be movable by means of e.g. being provided with wheels or being mounted on a table provided with wheels.

It shall be appreciated that the preferred embodiments described above with reference to FIGS. 3-5 are merely chosen to exemplify the antenna structures that may be used in the present invention. There are a large variety of other antenna devices, which can be used in the present invention.

It shall still further be appreciated that the medical transceiver device may be provided with further electrically conductive structures with separate feedings. Thus, such a medical transceiver device may be adapted for transmitting and/or receiving radio frequency waves in at least two different frequency bands, e.g. both around 400 MHz and around 2.4 GHz.

Although modifications and changes may be suggested by those skilled in the art, it is the invention of the inventors to embody within the patent warranted heron all changes and

We claim as our invention:

1. A medical transceiver device for radio-based communication with an implantable medical device comprising;
   circuitry for transmitting radio frequency signals to, and/or receiving radio frequency signals from, said implantable medical device, said radio frequency signals having a wavelength;
   first and second dipole antennas each having a structural length;
   an antenna feed network operatively interconnected between said circuitry and said first and second dipole antennas;
   each of said first and second dipole antennas being operable by said circuitry as a transmitting and/or receiving antenna for said radio frequency signals;
   said first and second dipole antennas being operable by said circuitry to emit and/or receive radio waves of different polarizations and thereby exhibiting polarization diversity; and
   said first and second dipole antennas being adjacent to each other at substantially a single location in space at a distance from each other of a size that is no larger than one-sixteenth of said wavelength, said size of said distance giving said first and second dipole antennas substantially no spatial diversity.

2. The medical transceiver device of claim 1 wherein said first and second dipole antennas are operable with said circuitry to emit and/or receive radio waves having essentially orthogonal polarizations.

3. The medical transceiver device of claim 1 wherein said circuitry receives radio frequency signals from said implantable medical device, and said first and second dipole antennas are operable with said circuitry as receiving antennas for said radio frequency signals.

4. The medical transceiver device of claim 3 comprising:
   a measuring unit that measures a signal quality parameter of said received radio frequency signals as received by each of said first and second dipole antennas; and
   a selecting unit configured to select either one or both of said first and second dipole antennas for subsequent reception of radio frequency signals depending on the measured signal quality parameter of said radio frequency signals as received by each of said first and second dipole antennas.

5. The medical transceiver device of claim 4 wherein said selecting means unit is configured to select the one of said first and second dipole antennas that receives the best signal quality parameter for said subsequent reception of radio frequency signals.

6. The medical transceiver device of claim 3 comprising,
   a receiver that receives from said implantable medical device a measure of a signal quality parameter of radio frequency signals as received by said implantable medical device, said radio frequency signals received by said implantable medical device being said radio frequency signals as transmitted to said implantable medical device after having been distorted by a transmission medium, and
   a selecting unit configured to select either one of said first and second dipole antennas for transmission of radio frequency signals depending on said received measure of the signal quality parameter of the radio frequency signals as received by said implantable medical device.

7. The medical transceiver device of claim 3 comprising:
   a detector that detects a signal quality parameter of the radio frequency signals as received by each of the first and second dipole antennas; and
   a summing unit that forms a weighted sum of the radio frequency signals received by the first and second dipole antennas based on the measured signal quality parameter of the received radio frequency signals.

8. The medical transceiver device of claim 3 comprising:
   a phase measurement unit that measures a phase of said radio frequency signals as received by each of said first and second dipole antennas; and
   a phase shifter that phase shifts the radio frequency signals received by the first and second dipole antennas to obtain a 0° phase difference between the he radio frequency signals.

9. The medical transceiver device of claim 1 wherein said circuitry transmits radio frequency signals to said implantable medical device, and said first and second dipole antennas are operable with said circuitry as transmitting antennas for said radio frequency signals.

10. The medical transceiver device of claim 9 comprising:
    a measuring unit that measures a signal quality parameter and a phase of said radio frequency signals as received by each of said first and second dipole antennas; and
    a selecting unit configured to select either one of said first and second dipole antennas for transmission of radio frequency signals depending on the measured signal quality parameter of said radio frequency signals as received by each of said first and second dipole antennas.

11. The medical transceiver device of claim 10 wherein said selecting unit is configured to select the one of said first and second dipole antennas that receives the best signal quality parameter for said subsequent transmission of radio frequency signals.

12. The medical transceiver device of claim 9 comprising
    a detector that details a signal quality parameter of the radio frequency signals received by each of said first and second dipole antennas; and
    an altering unit that alters a signal strength of the radio frequency signals as transmitted by at least one of said first and second dipole antennas depending on the measured signal quality parameter of said radio frequency signals received by each of said first and second dipole antennas.

13. The medical transceiver device of claim 12 wherein:
    a phase measurement unit that measures, as said signal quality parameter, a phase of said radio frequency signals received by each of said first and second dipole antennas; and
    said altering unit is a phase altering unit configured to alter a phase of the radio frequency signals transmitted by at least one of said first and second dipole antennas depending on the measured signal phases of said radio frequency signals received by each of said first and second dipole antennas.

14. The medical transceiver device of claim 13 wherein said phase altering unit is configured to alter the signal strength and the phase of the transmitted radio frequency signals to produce a combined output of said radio frequency signals as transmitted by said first and second dipole antennas, which has a polarization similar to the polarization of a combined input of said radio frequency signals received by said first and second dipole antennas.

15. The medical transceiver device of claim 12 comprising:
    a receiver that receives from said implantable medical device a measure of a signal quality parameter of radio frequency signals received by said implantable medical device, said radio frequency signals received by said implantable medical device being said radio frequency signals transmitted to said implantable medical device after having been distorted by a transmission medium, and wherein said altering unit is a signal strength altering unit that alters a signal strength or a phase of a subsequent transmission of radio frequency signals by at least one of said first and second dipole antennas depending on said received measure of the signal quality parameter of the radio frequency signals received by said implantable medical device.

16. The medical transceiver device of claim 1 wherein said different polarizations are linear polarizations.

17. The medical transceiver device of claim 1 wherein said first and second dipole antennas have at least one electrically conductive element in common.

18. The medical transceiver device of claim 17 wherein said first and second dipole antennas are identical except for having differently located connection points to said antenna network.

19. The medical transceiver device of claim 1 wherein each of said dipole antennas is a serpentine wire or a strip formed into an inductive electrically conductive structure.

20. The medical transceiver device of claim 1 wherein each of said dipole antennas comprises a linear structure.

21. The medical transceiver device of claim 20 wherein each of said linear structures comprises two elongated, parallel elements.

22. The medical transceiver device of claim 20 wherein said linear structures are arranged in a crossed relationship.

23. The medical transceiver device of claim 20 wherein each of the linear structures has a center of mass located along a straight line orthogonal to plane containing the linear structures.

24. The medical transceiver device of claim 23 wherein the linear structures are separated by a thin layer of a dielectric material.

25. The medical transceiver device of claim 1 wherein
said circuitry generates said radio frequency signals as unbalanced signals;
each of said first and second dipole antennas operates as a balanced antenna; and
said antenna feed network comprises a balun that converts said unbalanced signals to balanced signals.

26. The medical transceiver device of claim 1 wherein said antenna feed network comprises a microstrip transmission line.

27. The medical transceiver device of claim 1 comprising a single circuit board on which said circuitry, said first and second dipole antennas, and said antenna feed network are located.

28. The medical transceiver device of claim 1 wherein said first and second dipole antennas are movable as a unit to promote said spatial diversity.

29. The medical transceiver device of claim 1 comprising a third dipole antenna, said third dipole antenna being operatively connected to said antenna feed network, and being operable by said circuitry as a transmitting and/or receiving antenna for said radio frequency signals, and to emit and/or receive radio waves having a polarization, which is different from the polarizations of the radio waves emitted and/or received by said first and second dipole antennas.

30. The medical transceiver device of claim 29 wherein said third dipole antenna is operable by said circuitry to emit and/or receive radio waves having a polarization essentially orthogonal to the polarizations of the radio waves emitted and/or received by said first and second dipole antennas.

31. The medical transceiver device of claim 29 wherein said third dipole antenna is located adjacent said first and second dipole antennas at said single location.

32. A method for radio-based communication with an implantable medical device comprising the steps of:
receiving radio frequency signals from an implantable medical device via first and second antenna structures that are maximally sensitive to radio waves of different polarizations and operable adjacent each other at substantially a single location in space, each of said antenna structures having a structural length, and said radio waves having a wavelength;
at said substantially single location in space, placing said antenna structures at a distance from each other of a size that is no larger than either said structural length or one-quarter of said wavelength and thereby giving said first and second antenna structures a spatial diversity that is independent of said sensitivity to radio waves of different polarizations;
analyzing said radio frequency signals received via said first and second antenna structures;
from said analysis, determining a polarization state of said radio frequency signals received via said first and second antenna structures;
transmitting radio frequency signals to said implantable medical device via said first and second antenna structures; and
selecting at least one of an amplitude or a phase of said radio frequency signals transmitted via said first antenna structure relative to the amplitude or phase of said radio frequency signals transmitted via said second antenna structure depending on said determined polarization state.

33. A medical transceiver device for radio-based communication with an implantable medical device comprising:
circuitry for transmitting radio frequency signals to, and/or receiving radio frequency signals from, said implantable medical device;
first and second dipole antennas;
an antenna feed network operatively interconnected between said circuitry and said first and second dipole antennas;
each of said first and second dipole antennas being operable with said circuitry as a transmitting and/or receiving antenna for said radio frequency signals;
said first and second dipole antennas being operable by said circuitry to emit and/or receive radio waves of different polarizations and thereby exhibiting polarization diversity; and
said first and second dipole antennas being separated by a distance that is less than a maximum length of either one of said first and second dipole antennas, said distance giving said first and second dipole antennas substantially no spatial diversity.

34. A medical transceiver device for radio-based communication with an implantable medical device comprising:
circuitry for transmitting radio frequency signals to, and/or receiving radio frequency signals from, said implantable medical device, said radio frequency signals having a wavelength;
first and second dipole antennas;
an antenna feed network operatively interconnected between said circuitry and said first and second dipole antennas;

each of said first and second dipole antennas being operable by said circuitry as a, transmitting and/or receiving antenna for said radio frequency signals;

said first and second dipole antennas being operable by said circuitry to emit and/or receive radio waves of different polarizations; and said first and second dipole antennas being separated by a distance that is less than one-sixteenth of the wavelength of said radio frequency signals, said distance giving said dipole antennas substantially no spatial diversity.

35. A medical transceiver device for radio-based communication with an implantable medical device comprising:

circuitry for transmitting radio frequency signals to, and/or receiving radio frequency signals from, said implantable medical device;

first and second dipole antennas;

an antenna feed network operatively interconnected between said circuitry and said first and second dipole antennas;

each of said first and second dipole antennas being operable by said circuitry as a transmitting and/or receiving antenna for said radio frequency signals;

each of said first and second dipole antennas comprising two elongated elements parallel with each other; and said first and second dipole antennas being arranged at a distance there between in a crossed relationship, essentially orthogonally to each other, said distance and said crossed relationship giving said first and second dipole antennas polarization diversity and substantially no spatial diversity.

36. The medical transceiver device of claim 35 wherein each of said first and second dipole antennas is a serpentine wire.

37. The medical transceiver device of claim 35 each of said first and second dipole antennas has a center of mass located along a straight line orthogonal to a plane containing said first and second dipole antennas.

38. The medical transceiver device of claim 35 wherein said first and second dipole antennas are separated by a layer of dielectric material.

39. A medical communication system comprising:

an extracorporeal device selected from the group consisting of programmers and patient monitoring devices;

an implantable medical device comprising a radio transmitter and/or receiver; and a medical transceiver device in said extracorporeal device, said medical transceiver device comprising circuitry for transmitting radio frequency signals, having a wavelength, to, and/or receiving radio frequency signals from, said implantable medical device, first and second dipole antennas—each having a structural length, an antenna feed network operatively interconnected between said circuitry and said first and second dipole antennas, each of said first and second dipole antennas being operable by said circuitry as a transmitting and/or receiving antenna for said radio frequency signals, said first and second dipole antennas being operable with said circuitry to emit and/or receive radio waves of different polarizations and thereby exhibiting polarization diversity, and said first and second dipole antennas being adjacent to each other substantially at a single location in space at a fixed distance from each other of a size that is no larger than one-sixteenth of said wavelength, said size of said distance giving said dipole antennas substantially no spatial.

40. The medical communication system of claim 39 wherein said medical transceiver device is a portable device, and communicates with the extracorporeal device via a connection selected from the group consisting of wire connections and wireless connections.

41. The medical communication system of claim 40 wherein said portable unit comprises a processor and memory in order to communicate with said device via a wireless communication selected from the group consisting of USB, Bluetooth, and infrared connections.

* * * * *